United States Patent [19]

Gayler et al.

[11] 4,100,796
[45] Jul. 18, 1978

[54] TEST APPARATUS

[75] Inventors: Joachim Gayler; Rolf Remy; Werner Moeller; Fritz G. Holler, all of Wuppertal, Germany

[73] Assignee: Akzona Incorporated, Asheville, N.C.

[21] Appl. No.: 846,048

[22] Filed: Oct. 27, 1977

[51] Int. Cl.² ............................ G01N 3/34; G01N 3/36
[52] U.S. Cl. .................................... 73/160; 73/432 SD
[58] Field of Search .......... 73/160, 159, 95.5, 432 SD, 73/97, 95

[56] References Cited

U.S. PATENT DOCUMENTS 2,242,889  5/1941  Keeler .................................. 73/160
2,407,545  9/1946  Fish ..................................... 73/160

OTHER PUBLICATIONS

Dupont; Research Disclosure; Apr. 1977; Interlace Measuring Instrument; p. 18.

Primary Examiner—S. Clement Swisher
Assistant Examiner—Denis E. Corr
Attorney, Agent, or Firm—Francis W. Young; Tom R. Vestal

[57] ABSTRACT

Yarn testing device comprising a spool, a variably driven godet with one yarn coil, followed by a suction nozzle, and a yarn tensioner to switch on and off, located between the spool and the godet, the suction nozzle and the pneumatically actuated yarn tensioner being connected with a changeover switch.

3 Claims, 2 Drawing Figures

TEST APPARATUS

BACKGROUND OF THE INVENTION

The innovation relates to a device to test the runoff behavior from yarn packages of certain yarns intended especially for the weaving sector, comprising a variably driven godet to draw off the yarn from the spool, on which godet the yarn is given a 360° turn, a suction jet mounted in the yarn travel direction behind the godet and an on or off yarn tension located between spool and godet.

A similar device is described, for example, in the periodical "Textile Praxis International", June 1975, p. 687 and following in the paragraph "Optimale Wicklungen fur Texturgarne" by P. Dubach. With this known device which is intended to aid the formation of yarn packages for weaving textured yarns, it is possible to simulate draw-off processes at rates of up to 1500m/min., either continuously or discontinuously (like the weaving process). The yarn draw-off element of this known device is composed of a pair of rollers including a bottom roll (godet) rotating at constant circumferential speed and an upper roll mounted on the armature of a vibrator, which applies pressure steadily (continuous draw-off) or intermittently (discontinuous draw-off) to the bottom roll.

Due to the clamping force of the two rollers, the yarn is pulled through in the direction of rotation. For a continuous draw-off, the yarn is given one turn (360° C) on the bottom roll, to insure absolutely slippage-free pull-through. The suction jet is used to pick up the yarn, otherwise the yarn to be drawn off would wrap around the roller. During this continuous draw-off, the armature with the upper roller is imparted an up and down movement at adjustable cycles by means of an oscillator with amplifier. Thereby, the upper roller is forced down on the bottom roller for the duration of a square wave impulse and together with the yarn between said rollers is accelerated to the circumferential speed of the bottom roller (godet). The yarn tension located between godet and spool grips the yarn during the ascending movement of the upper roller so that it will actually assume a velocity 0 during the stop phase.

The known device presents considerable drawbacks, especially in discontinuous operation when used as filling simulator. Reduction of the yarn velocity to 0 or rapid acceleration of the yarn to the circumferential speed of the bottom roller (godet) poses problems, especially at higher on and off frequencies. Moreover, the known device allows draw-off speeds of only up to 1500 m/min.

The objective of this innovation is the further development of a device of the above described type to the extent that even at high on and off frequencies of 20 to 30 sec$^{-1}$, reduction of the yarn velocity to 0 or rapid acceleration of the yarn to the circumferential speed of the godet would be insured. Furthermore, the device according to the innovation should allow draw-off speeds to about 2500 m/min.

This objective is achieved according to the innovation by means of a changeover switch connected with the suction jet and the pneumatically actuated yarn tension.

In the device of the invention, the godet — as in the known device — runs at an adjustable but constant circumferential speed and the yarn is given one turn on it (angle of contact about 360° C). When the suction jet is actuated, an instantaneous "rope friction effect" or Servo effect sets in, accelerating the yarn practically without perceptible delay to the circumferential speed of the godet, at which speed it is withdrawn from the spool. The draw-off force of the godet ($S_2$) is always proportional to the compressed-air-adjustable draw-off force of the suction jet ($S_1$). The following correlation exists between $S_1$ and $S_2$ (Eytelwein formula):

$$S_2 = S_1 \cdot e^{\mu \alpha}$$

wherein
$e$ = 2.781 (natural logarithm base)
$\mu$ = coefficient of friction between yarn and godet
$\alpha$ = angle of contact of the yarn on the godet e.g. = $2\pi$ at an angle of contact of 360°.

Since the maximum draw-off force $S_2$ can be adjusted by means of the compressed air actuating the suction jet, it is possible for the first time to have a draw-off device with an accurately adjusted draw-off force, which force can be substantially smaller than the breaking force of the material to be investigated, whereby the precision of the yarn travel is nevertheless insured. It is thus possible to locate on a yarn package winding defects or impairments interfering with unwinding, since the yarn being drawn off does not necessarily break nor does the winding interference yield to force, but rather the yarn travel is interrupted so that the cause of the malfunction can easily be detected on the yarn package.

As the suction jet is actuated, the yarn tension is turned off, i.e., deactivated, so that the yarn reaches the godet without tension. When the suction jet is deactivated, the changeover switch immediately actuates the pneumatically controlled yarn tension. The yarn is thereby efficiently decelerated to 0.

Since, in principle, commercial yarn tensions are not used to decelerate the passing yarn to 0 in a minimum of time, the innovation proposes a yarn tension making possible an especially rapid tensioning of the yarn. This preferred version of a yarn tension comprises a first, stationary tension disc and a second pneumatically actuated tension disc moving in contact with the former. The innovation is explained on hand of enclosed drawings.

DETAILED DESCRIPTION OF THE DRAWINGS

Figure 1:
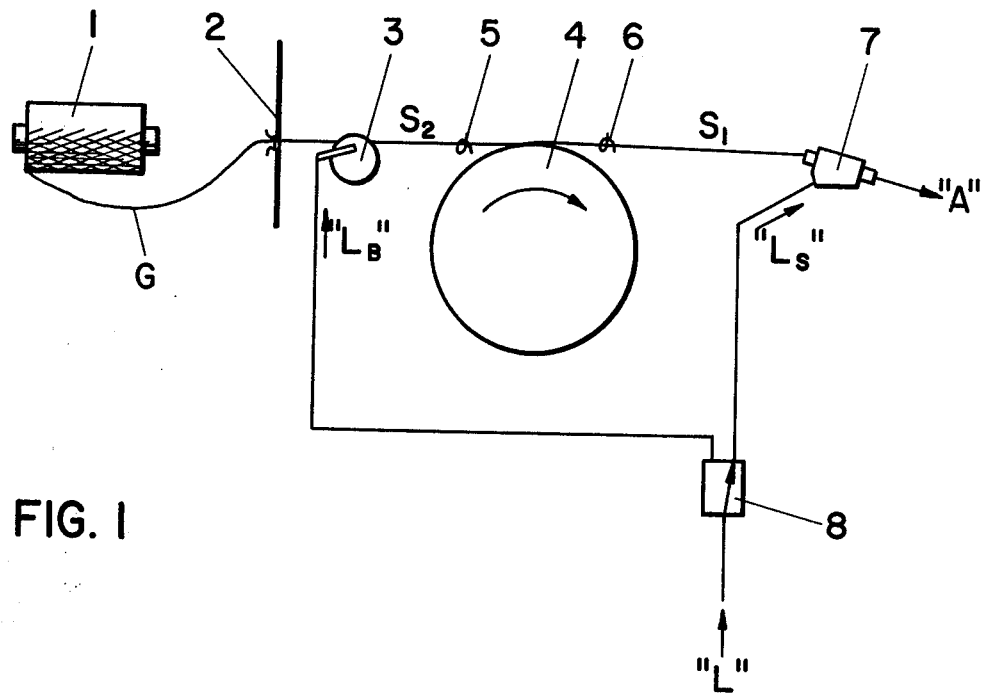
FIG. 1 is a schematic drawing of a device according to the innovation.

As shown in FIG. 1, a yarn G, for example a textured yarn intended for weaving, is drawn off spool 1 via thread guide 2 by godet 4 at a draw-off force $S_2$; thereby, the yarn travels through a yarn tension 3 and is given a turn of about 360° C on godet 4 driven at constant velocity, whereby thread guides 5 and 6 insure that the yarn sections traveling on or off the godet do not come in mutal contact. The entrainment of the yarn by the godet is initiated by means of a rope friction-induced instantaneous Servo effect by suction jet 7 operated at a draw-off force $S_1$, virtually without time lag, at the moment at which it is actuated by compressed air. A changeover switch 8 insures that the air current flowing in the direction of arrow "L" is either fed to yarn tension 3 via line "$L_B$" or to the suction jet via line "$L_S$". In the illustrated situation, yarn tension 3 has just been deactivated, while the yarn is being drawn off suction jet 7 in the direction of arrow "A", for example, into a waste can.

An impulse transmitter actuating changeover switch 8 at the required frequency is not shown.

Instead of a single air line branching off at changeover switch 8, it is, of course, also possible to use separate lines for yarn tension and suction jet, said lines operating at different pressures and being equipped with alternately opening and closing valves.

Figure 2:
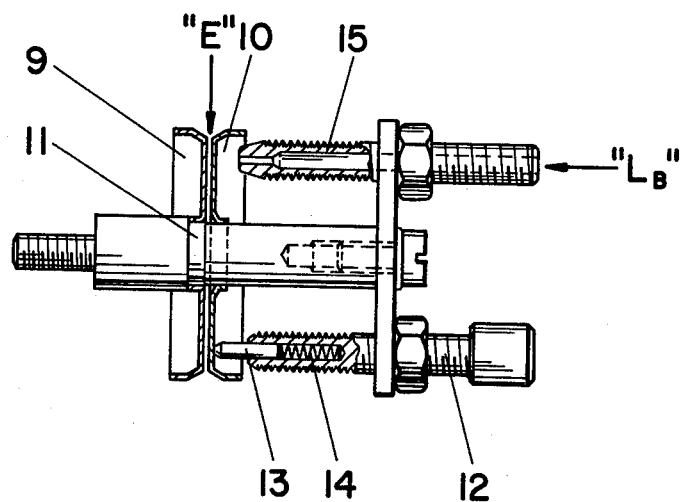
FIG. 2 is a sectional drawing of the preferred yarn tension.

FIG. 2 illustrates a preferred version of the yarn tension. It is essentially composed of a stationary first tension disc 9 mounted on pin 11 and a second tension disc 10 slipped with tolerance on pin 11 and movable against the first tension disc 9, with the lower ranges of tension disc 10 capable of being held at a certain pressure against tension disc 9 via screw 12 and bolt 13 pretensioned by spring 14, as a result of which the normally parallel tension disc planes are tilted toward one another under formation of a narrow, wedge-shaped slit. The yarn is placed in the slit in the direction of arrow "E". When the yarn tension is deactivated (as shown) the yarn can travel without interference through the slit. When the suction jet is deactivated and the yarn tension actuated, jet 15 and line "$L_B$" receive compressed air. The air streaming from jet 15 forces the upper part of tension disc 10 against stationary tension disc 9 thereby gripping the yarn traveling in the slit between the two tension discs, and decelerating it in the process to 0.

When the compressed air supply to jet 15 is interrupted, tension disc 10 resumes the illustrated position and releases the yarn.

The device according to the innovation is suitable both for continuous runoff tests which are merely aimed at investigating the draw-off behavior of yarns of specific put up at specific velocities. The device is especially suitable for discontinuous unwinding experiments simulatting filling insertion on weaving machines which alternate constantly between acceleration to full speed and deceleration to 0 speed.

What is claimed is:

1. An improvement in yarn test devices including a yarn package supply, an adjustable drive godet, and a yarn suction device in series; the improvement comprising an intermittantly operable yarn tensioning device located between the yarn package supply and drive godet and means for alternately actuating the yarn suction device and the yarn tensioning device to accelerate and decelerate a yarn being tested between a full running condition and a full stop condition.

2. The improvement in yarn test devices of claim 1, wherein the yarn tensioning device comprises a first stationary disc and second movable disc, yarn guides located on each side of the discs in a line with the mating surfaces of the discs, and wherein the means for alternately actuating the yarn suction device and yarn tensioning device include means for moving the second disc toward the first disc when the yarn suction device is inactivated.

3. The improvement in yarn test devices of claim 2, wherein the means for moving the second disc toward the first disc includes a pneumatic tow-position switch having a running position outlet and a tension position outlet, a pneumatic gas supply to the switch, a nozzle located adjacent and directed toward the second disc opposite the first disc, and a pneumatic line connecting the tension position outlet of the pneumatic switch and the nozzle, whereby when the tension position of the switch is activated, gas from the supply passes through the line and nozzle, urging the second disc against the first disc.

* * * * *